US012797129B2

(12) United States Patent
Chatzizisis

(10) Patent No.: US 12,797,129 B2
(45) Date of Patent: Nov. 17, 2026

(54) PATIENT-SPECIFIC COMPUTATIONAL SIMULATION OF CORONARY ARTERY BYPASS GRAFTING

(71) Applicant: Board of Regents of the University of Nebraska, Lincoln, NE (US)

(72) Inventor: Ioannis S. Chatzizisis, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1225 days.

(21) Appl. No.: 17/743,178

(22) Filed: May 12, 2022

(65) Prior Publication Data

US 2022/0378506 A1 Dec. 1, 2022

Related U.S. Application Data

(60) Provisional application No. 63/194,084, filed on May 27, 2021.

(51) Int. Cl.
*A61B 34/10* (2016.01)
*G06T 7/00* (2017.01)
(Continued)

(52) U.S. Cl.
CPC ............ *A61B 34/10* (2016.02); *G06T 7/0012* (2013.01); *G06T 7/11* (2017.01); *G06T 17/20* (2013.01);
(Continued)

(58) Field of Classification Search
None
See application file for complete search history.

(56) References Cited

U.S. PATENT DOCUMENTS 9,349,178 B1 * 5/2016 Itu .......................... G16H 50/20
2010/0017171 A1 * 1/2010 Spilker .................. G16H 30/40
703/2

(Continued)

FOREIGN PATENT DOCUMENTS

WO WO-2013192234 A1 * 12/2013 ............ G16Z 99/00

OTHER PUBLICATIONS

International Search Report and Written Opinion for PCT/US22/29036 mailed Aug. 10, 2022.

*Primary Examiner* — Katherine L Fernandez
(74) *Attorney, Agent, or Firm* — Foley Hoag LLP; Erik A. Huestis; Joshua S. Matloff

(57) ABSTRACT

In accordance with embodiments of this disclosure, a computational simulation platform for assessing impact of coronary artery bypass grafting comprises a computer-implemented method that includes: generating patient-specific three-dimensional (3D) reconstructions of path lines for a patient's heart, ascending aorta, aortic arch, descending thoracic aorta, great vessels, coronary arteries and their major branches based on noninvasive imaging; performing virtual CABG by modifying the patient-specific 3D reconstructions to computationally add path lines for one or more bypass grafts; performing post-virtual CABG computational fluid dynamic (CFD) studies under computational resting and stress conditions; and assessing hemodynamic impact of virtual CABG on the resting and hyperemic flow of diseased native coronary arteries and virtual bypass grafts.

15 Claims, 2 Drawing Sheets

(51) Int. Cl.
*G06T 7/11* (2017.01)
*G06T 17/20* (2006.01)
*G06T 19/20* (2011.01)

(52) U.S. Cl.
CPC ........ *G06T 19/20* (2013.01); *A61B 2034/104* (2016.02); *A61B 2034/105* (2016.02); *G06T 2200/04* (2013.01); *G06T 2207/30048* (2013.01); *G06T 2207/30104* (2013.01); *G06T 2219/2004* (2013.01)

(56) References Cited

U.S. PATENT DOCUMENTS

2013/0132054 A1* 5/2013 Sharma .................. G16H 30/40
703/9
2020/0188029 A1 6/2020 Taylor

* cited by examiner

PATIENT-SPECIFIC COMPUTATIONAL SIMULATION OF CORONARY ARTERY BYPASS GRAFTING

CROSS-REFERENCE TO RELATED APPLICATIONS

The present application claims priority under 35 U.S.C. § 119(e) to U.S. Provisional Application Ser. No. 63/194,084, filed May 27, 2021, and titled "Patient-Specific Computational Simulation of Coronary Artery Bypass Grafting," which is incorporated herein by reference in its entirety.

TECHNICAL FIELD

The present invention generally relates to systems and methods for simulating and assessing impact of coronary artery bypass grafting.

BACKGROUND

Coronary artery disease (CAD) is a common condition affecting millions of people worldwide. Treatment of CAD with coronary artery bypass graft surgery (CABG) depends on bypassing severe coronary artery stenoses using arterial or vein grafts. CABG is the most commonly performed cardiac surgery throughout the world and provides survival benefit over percutaneous interventions or medical therapy alone in patients with anatomically complex CAD (Class I recommendation). The long-term success of CABG depends on the patency of bypass grafts, with 10-year patency ranging from 50% for vein grafts up to 95% for internal mammary artery grafts. Graft failure depends on the graft type and the local hemodynamic conditions of the native coronary artery and bypass graft, among other factors. Compared to arterial grafts, vein grafts are more prone to neointimal hyperplasia, which is the main mechanism of their failure. Flow in the grafted native coronary artery also affects graft (primarily arterial) patency. Non-hemodynamically significant native coronary stenoses allow for greater flow through native circulation, diminishing the flow through the bypass graft, ultimately resulting in graft dysfunction and failure.

Although the impact of the severity of native artery stenosis upon graft patency is well recognized clinically and forms the basis for CABG guidelines, these recommendations rely upon visual interpretations of coronary stenoses by invasive angiography that suffers from high inter- and intra-observer variability. Quantitative coronary angiography could potentially limit these effects, but it does not correlate well with the hemodynamic significance of a lesion. Conventionally, an angiographic stenosis of greater than 70% luminal diameter is considered anatomically significant. However, over 50% of these lesions are not associated with myocardial ischemia. Fractional flow reserve (FFR) has been proposed as the invasive gold standard for the identification of ischemic lesions. FFR is defined as the ratio of mean pressure distal to the stenosis (measured by the pressure wire) over the mean aortic pressure (measured at the tip of the guiding catheter) under hyperemic conditions, mostly induced with vasodilators. An FFR-guided strategy of percutaneous revascularization using the FFR ischemic cut-off of 0.80 has been shown to be superior to the invasive angiography-guided approach. Interestingly, there is significant heterogeneity regarding the presence of ischemia in angiographically non-critical stenoses (i.e. 50-90%). 35% of angiographically moderate (50-70%) stenoses have an ischemic FFR≤0.80, 80% of angiographically significant stenoses (71-90%) have an ischemic FFR≤0.80, and 96% of angiographically critical stenoses (>90%) have an ischemic FFR≤0.80. In clinical practice, FFR is used sparingly because it requires additional procedural time, expertise, and exposure to intravenous contrast and radiation, therefore increasing the procedural risk. Moreover, the pressure wire is difficult to maneuver in complex coronary lesions, and extensive handling can damage its sensors and reduce the accuracy of measurements. Non-hyperemic pressure ratios (e.g., instantaneous flow ratio) are considered at least equal to FFR but involve similar risks to invasive wire-based FFR measurement. Angiographic FFR is an accurate alternative to invasive wire-based indices but requires an invasive approach.

Application of computational fluid dynamics (CFD) studies derived from coronary computed tomographic angiography (CCTA) has emerged as a non-invasive tool to assess the hemodynamic significance of coronary artery disease (e.g., $FFR_{CT}$, HeartFlow, Redwood City, California, USA). Furthermore, CCTA-based CFD has been used for the assessment of local hemodynamics in the native coronary arteries and bypass grafts. To date, most of the computational investigations of bypass surgery have been focused on the effect of graft type, graft configuration and anastomosis geometry on the local hemodynamics.

The concept of combining non-invasive anatomical imaging (e.g., CCTA) with CFD analysis to computationally test the hemodynamic effectiveness of bypass grafting and assist in the surgical planning is enticing and warrants further investigation. The ability to accurately, and noninvasively, predict post-CABG hemodynamics may have significant impact on the clinical practice of CABG by enabling a surgeon to tailor the surgical plan (graft number and types) to each individual patient and achieve the best possible graft patency and outcomes.

SUMMARY

A computational simulation platform for assessing impact of coronary artery bypass grafting is disclosed. In embodiments, the computational simulation platform comprises a computer-implemented method that includes: generating patient-specific three-dimensional (3D) reconstructions of path lines for a patient's heart, ascending aorta, aortic arch, descending thoracic aorta, great vessels, coronary arteries and their major branches based on noninvasive imaging; performing virtual CABG by modifying the patient-specific 3D reconstructions to computationally add path lines for one or more bypass grafts; performing post-virtual CABG computational fluid dynamic (CFD) studies under computational resting and stress conditions; and assessing hemodynamic impact of virtual CABG on the resting and hyperemic flow of diseased native coronary arteries and virtual bypass grafts.

In some embodiments of the computational simulation platform, the noninvasive imaging comprises computed tomography angiography or magnetic resonance angiography.

In some embodiments of the computational simulation platform, lumen boundaries for the path lines are segmented and lofted to create patient-specific geometries of heart, aorta, coronaries and great vessels.

In some embodiments of the computational simulation platform, the patient-specific 3D reconstructions and virtual bypass grafts are discretized into a fine mesh near lumen walls.

In some embodiments of the computational simulation platform, the patient-specific 3D reconstructions and virtual bypass grafts employ a three-element Windkessel model for non-coronary outlets to model parameters for resistance and capacitance of proximal vessels and resistance of distal vessels.

In some embodiments of the computational simulation platform, the patient-specific 3D reconstructions and virtual bypass grafts employ a lumped parameter model for coronary outlets to model parameters for coronary arterial resistance, coronary arterial microcirculation resistance, coronary venous microcirculation resistance, coronary venous resistance, coronary arterial compliance, myocardial compliance, and intramyocardial pressure.

In some embodiments of the computational simulation platform, the patient-specific 3D reconstructions and virtual bypass grafts are configured to computationally simulate hyperemic conditions.

In some embodiments of the computational simulation platform, a resting flow rate is extrapolated by shortening its diastolic portion and shifting the resting flow rate up to extrapolate a simulated hyperemic waveform.

In some embodiments of the computational simulation platform, the extrapolated simulated hyperemic waveform is prescribed at an aortic inlet.

In some embodiments of the computational simulation platform, the computer-implemented method further includes: calculating flow parameters in the native coronary arteries and virtual bypass grafts.

A system for assessing impact of coronary artery bypass grafting (CABG) is also disclosed. In embodiments, the system includes one or more medical imaging devices and one or more computer systems communicatively coupled to the one or more medical imaging devices. The one or more computer systems may be configured to: generate patient-specific three-dimensional (3D) reconstructions of path lines for a patient's heart, ascending aorta, aortic arch, descending thoracic aorta, great vessels, coronary arteries and their major branches based on noninvasive imaging data collected by the one or more medical imaging devices; perform virtual CABG by modifying the patient-specific 3D reconstructions to computationally add path lines for one or more bypass grafts; perform post-virtual CABG computational fluid dynamic (CFD) studies under computational resting and stress conditions; and assess hemodynamic impact of virtual CABG on the resting and hyperemic flow of diseased native coronary arteries and virtual bypass grafts.

In some embodiments of the system, the noninvasive imaging data comprises computed tomography angiography data or magnetic resonance angiography data.

In some embodiments of the system, lumen boundaries for the path lines are segmented and lofted to create patient-specific geometries of heart, aorta, coronaries and great vessels.

In some embodiments of the system, the patient-specific 3D reconstructions and virtual bypass grafts are discretized into a fine mesh near lumen walls.

In some embodiments of the system, the patient-specific 3D reconstructions and virtual bypass grafts employ a three-element Windkessel model for non-coronary outlets to model parameters for resistance and capacitance of proximal vessels and resistance of distal vessels.

In some embodiments of the system, the patient-specific 3D reconstructions and virtual bypass grafts employ a lumped parameter model for coronary outlets to model parameters for coronary arterial resistance, coronary arterial microcirculation resistance, coronary venous microcirculation resistance, coronary venous resistance, coronary arterial compliance, myocardial compliance, and intramyocardial pressure.

In some embodiments of the system, the patient-specific 3D reconstructions and virtual bypass grafts are configured to computationally simulate hyperemic conditions.

In some embodiments of the system, a resting flow rate is extrapolated by shortening its diastolic portion and shifting the resting flow rate up to extrapolate a simulated hyperemic waveform.

In some embodiments of the system, the extrapolated simulated hyperemic waveform is prescribed at an aortic inlet.

In some embodiments of the system, the one or more computer systems are further configured to: calculate flow parameters in the native coronary arteries and virtual bypass grafts.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Coronary artery bypass grafting (CABG) is a surgical intervention in patients with extensive obstructive coronary artery disease by invasive angiography. The present disclosure is directed to a novel application of computational fluid dynamics for non-invasive computational assessment of coronary hemodynamics and bypass grafts. In particular, a computational platform for simulating and assessing impact of CABG is disclosed with reference to FIGS. 1 and 2. Computational simulations provide a clinically impactful tool for effective pre-procedural planning using noninvasive hemodynamic assessment of stenoses.

The computational platform disclosed herein has been validated, and it was found that the computationally calculated fractional flow reserve (FFR) showed high agreement with the angiography-based FFR. In one study, multiscale computational fluid dynamics simulations of pre- and post-CABG were performed under simulated resting and hyperemic conditions in patient-specific anatomies 3D reconstructed from coronary computed tomography angiography. Different degrees of stenosis were computationally created in the left anterior descending artery, and it was demonstrated that the presently disclosed computational simulation platform can faithfully reproduce the hemodynamic effects of bypass grafting on the native coronary arteries. Increasing severity of native artery stenosis resulted in increasing flow through the graft and improvement of resting and hyperemic flow in the distal part of the grafted native artery.

This disclosure presents a comprehensive patient-specific computational platform that can simulate the hemodynamic conditions before and after CABG, and faithfully reproduce the hemodynamic effects of bypass grafting on the native coronary artery flow. The ability to accurately, and noninvasively, predict post-CABG hemodynamics may have significant impact on the clinical practice of CABG by enabling a surgeon to tailor the surgical plan (graft number and types) to each individual patient and achieve the best possible graft patency and outcomes.

Figure 1:
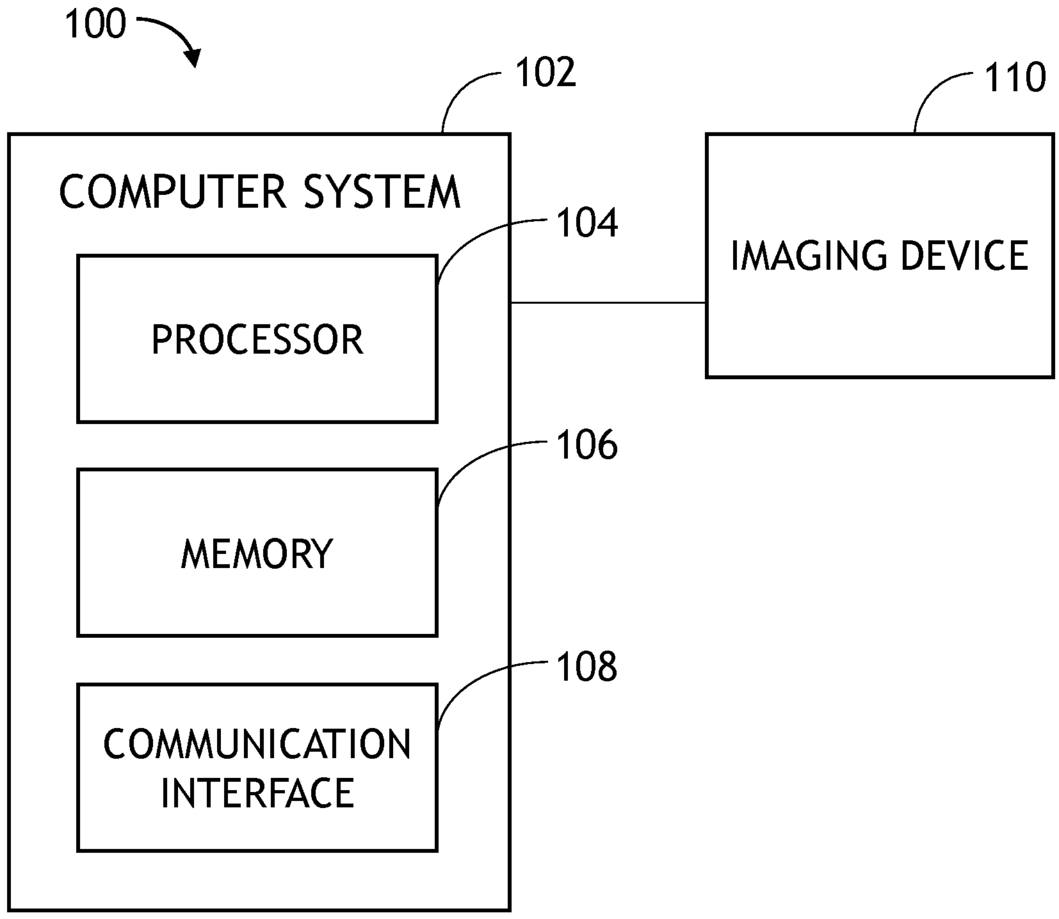
FIG. 1 is a block diagram illustrating a system for computationally simulating and assessing impact of coronary artery bypass grafting (CABG), in accordance with one or more embodiments of this disclosure.

FIG. 1 illustrates a system 100 for computationally simulating and assessing impact of CABG, in accordance with one or more embodiments of this disclosure. The system 100 includes one or more computer systems 102 (e.g., a computer, a plurality of computers performing different steps/processes, and/or a local or cloud computing cluster of computer systems working together sequentially or in parallel). The system 100 further includes one or more noninvasive medical imaging devices 110 that are communicatively coupled to the one or more computer systems 102. For example, the one or more medical imaging devices 110 may be physically connected (e.g., wired) to the one or more computer systems 102, wirelessly connected (e.g., via WiFi, WLAN, Bluetooth, or the like), and/or communicatively coupled by at least one portable storage device (e.g., USB drive, portable hard drive, or the like) that is configured to store data collected by the one or more medical imaging devices 110 so that the data can be transferred to the one or more computer systems 102.

Examples of a noninvasive medical imaging device 110 include, but are not limited to, a computed tomography (CT) scanner, a magnetic resonance imaging (MRI) machine, an X-ray scanner, a fluoroscope, an ultrasound scanner. In embodiments, the one or more noninvasive medical imaging devices 110 may include any number or combination forgoing devices.

The one or more computer systems 102 may be configured to implement the computational simulation platform by performing various functions, steps and/or operations discussed herein. In embodiments, a computer system 102 (or each computer system 102 of a cluster) includes at least one processor 104, memory 106 and communication interface 108.

The processor 104 provides processing functionality for at least the computer system 102 and can include any number of processors, microprocessors, microcontrollers, circuitry, field programmable gate array (FPGA) or other processing systems and resident or external memory for storing data, executable code and other information accessed or generated by the computer system 102. The processor 104 can execute one or more software programs embodied in a non-transitory computer readable medium (e.g., memory 106) that implement techniques/operations described herein. The processor 104 is not limited by the materials from which it is formed, or the processing mechanisms employed therein and, as such, can be implemented via semiconductor(s) and/or transistors (e.g., using electronic integrated circuit (IC) components), and so forth.

The memory 106 can be an example of tangible, computer-readable storage medium that provides storage functionality to store various data and/or program code associated with operation of the computer system 102/processor 104, such as software programs and/or code segments, or other data to instruct the processor 104, and possibly other components of the computer system 102, to perform the functionality described herein. Thus, the memory 106 can store data, such as a program of instructions for operating the computer system 102, including its components (e.g., processor 104, communication interface 108, etc.), and so forth. It should be noted that while a single memory 106 is described, a wide variety of types and combinations of memory (e.g., tangible, non-transitory memory) can be employed. The memory 106 can be integral with the processor 104, can comprise stand-alone memory, or can be a combination of both. Some examples of the memory 106 can include removable and non-removable memory components, such as random-access memory (RAM), read-only memory (ROM), flash memory (e.g., a secure digital (SD) memory card, a mini-SD memory card and/or a micro-SD memory card), solid-state drive (SSD) memory, magnetic memory, optical memory, universal serial bus (USB) memory devices, hard disk memory, external memory, and so forth.

The communication interface 108 can be operatively configured to communicate with components of the computer system 102. For example, the communication interface 108 can be configured to retrieve data from the processor 104 or other devices (e.g., medical imaging devices 110, other computer systems 102, local/remote servers, etc.), transmit data for storage in the memory 106, retrieve data from storage in the memory 106, and so forth. The communication interface 108 can also be communicatively coupled with the processor 104 to facilitate data transfer between components of the computer system 102 and the processor 104. It should be noted that while the communication interface 108 is described as a component of the computer system 102, one or more components of the communication interface 108 can be implemented as external components communicatively coupled to the computer system 102 via a wired and/or wireless connection. The computer system 102 can also include and/or connect to one or more input/output (I/O) devices (e.g., via the communication interface 108), such as an input device (e.g., a mouse, a trackball, a trackpad, a joystick, a touchpad, a touchscreen, a keyboard, a keypad, a microphone (e.g., for voice commands), etc.) and/or an output device (e.g., a display, a speaker, a tactile feedback device, etc.). In embodiments, the communication interface 108 may also include or may be coupled with a transmitter, receiver, transceiver, physical connection interface, or any combination thereof.

It shall be understood that any of the functions, steps or operations described herein are not necessarily all performed by one computer system 102. In some embodiments, various functions, steps or operations may be performed by one or more computer systems 102. For example, one or more operations and/or sub-operations may be performed by a first computer system, additional operations and/or sub-operations may be performed by a second computer system, and so forth. Furthermore, some of the operations and/or sub-operations may be performed in parallel and not necessarily in the order that they are disclosed herein.

Figure 2:
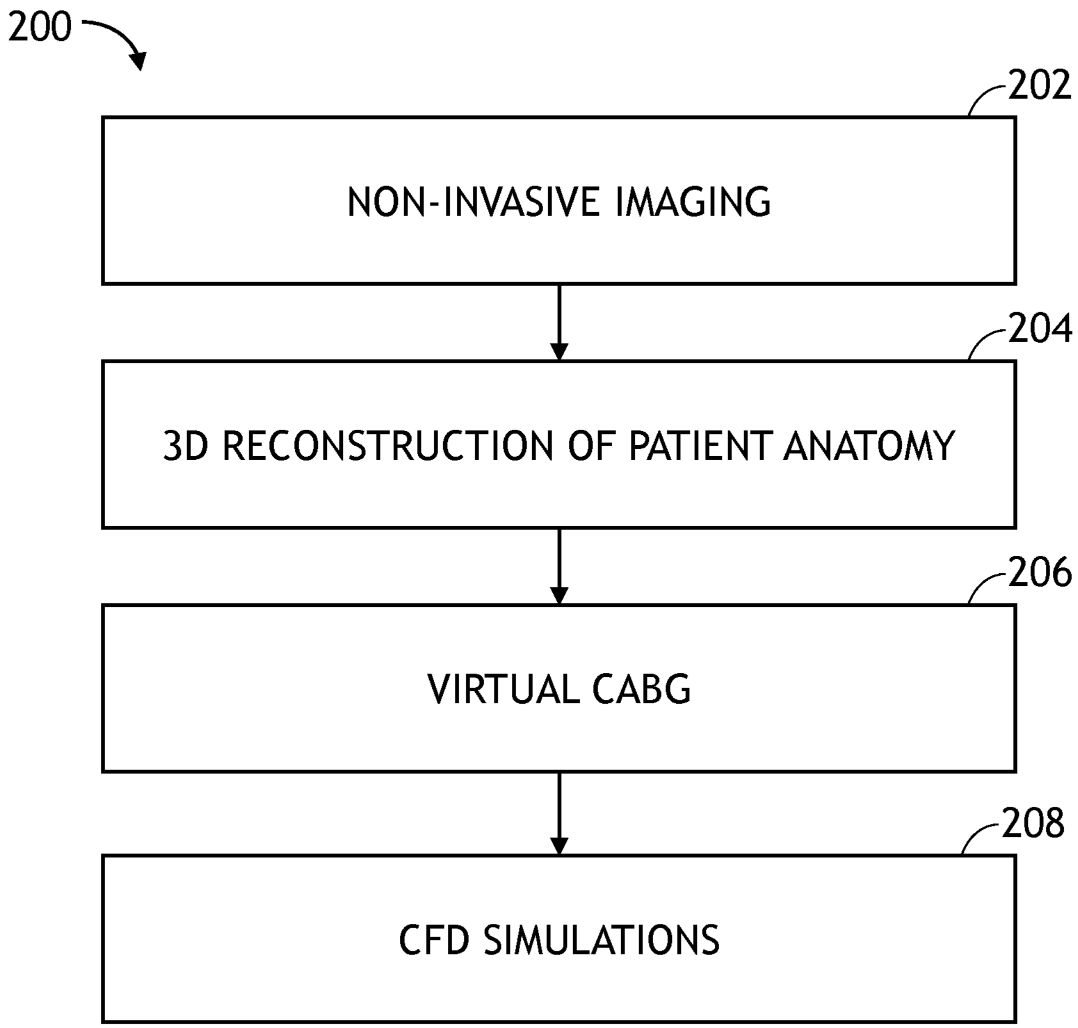
FIG. 2 is a flow diagram illustrating the methodology of a computational simulation platform that replicates the impact of CABG, in accordance with one or more embodiments of this disclosure.

FIG. 2 is a flow diagram illustrating a computational simulation platform 200 for computationally simulating and assessing impact of CABG. In embodiments, the computational simulation platform 200 is embodied by a computer-implemented method that includes the following blocks (e.g., functions, steps and/or operations).

At block 202, noninvasive imaging data is collected for one or more of patient's path lines, including, but not limited to the patient's heart, ascending aorta, aortic arch, descending thoracic aorta, great vessels, coronary arteries and their major branches. For example, the one or more computer systems 102, via the one or more imaging devices 110, may be configured to collect noninvasive imaging data via computed tomography angiography, magnetic resonance angiography, or the like. Additionally, the one or more computer systems 102, via the one or more imaging devices 110, may be configured to collect noninvasive imaging data for one or more of the patient's path lines using any of the tools and/or techniques described in the examples or embodiments discussed herein.

At block 204, a three-dimensional (3D) reconstruction of the patient's path lines is generated based on the noninvasive imaging data collected by the one or more imaging devices 110. For example, the one or more computer systems 102 may be configured to generate a 3D reconstruction of the patient's heart, ascending aorta, aortic arch, descending thoracic aorta, great vessels, coronary arteries and their major branches based on the noninvasive (e.g., CT or MRI) data. Additionally, the one or more computer systems 102 may be configured to generate the 3D reconstruction of the patient's path lines based on noninvasive imaging data collected by the one or more imaging devices 110 using any of the tools and/or techniques described in the examples or embodiments discussed herein.

At block 206, virtual CABG is performed by modifying the patient-specific 3D reconstructions that were generated at block 204 to computationally add path lines for one or more bypass grafts. For example, the one or more computer systems 102 may be configured to modify the previously generated patient-specific 3D reconstructions and/or generate new 3D reconstructions that include the patient's existing path lines with one or more simulated additional path lines (i.e., virtual bypass grafts) that are modeled based on the noninvasive imaging data and/or imported data associated with hemodynamic characteristics of the bypass grafts being simulated.

For the patient-specific 3D reconstructions and virtual bypass grafts, the one or more computer systems 102 may be configured to employ a three-element Windkessel model for non-coronary outlets to model parameters for resistance (Rp) and capacitance (C) of the proximal vessels and resistance (Rd) of the distal vessels. Additionally, the one or more computer systems 102 may be configured to employ a lumped parameter model for coronary outlets to model parameters for coronary arterial resistance ($R_a$), coronary arterial microcirculation resistance ($R_{a\text{-}micro}$), coronary venous microcirculation resistance ($R_{v\text{-}micro}$), coronary venous resistance ($R_v$), coronary arterial compliance ($C_a$), intramyocardial compliance ($C_{im}$), and intramyocardial pressure ($P_{im}$). The total resting resistance of all outlets may be calculated based on the ratio of mean aortic pressure to the mean flow rate. In some embodiments, the modified Murray's law may be employed to calculate the resistance of each coronary branch.

The lumen boundaries for the path lines may be segmented and lofted to create patient-specific geometries of heart, aorta, coronaries and great vessels, and the patient-specific 3D reconstructions and virtual bypass grafts may be discretized into a fine mesh (e.g., tetrahedral elements with three layers of fine mesh) near lumen walls. In some embodiments, to 3D reconstruct the post-CABG anatomy, the path lines of the ascending aorta, aortic arch, descending thoracic aorta, great vessels, coronary arteries (including their major branches) and bypass grafts may be extracted, and lumen boundaries may be segmented manually using vasculature simulation software. The segmented lumen contours may be lofted to create the 3D patient-specific lumen geometries. In an example embodiment, the 3D reconstructed lumen geometries are further discretized (e.g., into tetrahedral elements with three refined prism layers on the vessel lumen) using the vasculature simulation software. In some embodiments, 3D post-CABG anatomies are reconstructed from CCTA and computationally created focal lumen stenoses with multiple degrees of severity (e.g., mild, moderate, severe, critical). Additionally, the one or more computer systems 102 may be configured to virtual CABG by modifying the patient-specific 3D reconstructions to computationally add path lines for one or more bypass grafts using any of the tools and/or techniques described in the example or embodiments discussed herein.

At block 208, post-virtual CABG CFD studies under computational resting and stress conditions are performed and used to assess hemodynamic impact of virtual CABG on the resting and hyperemic flow of diseased native coronary arteries and virtual bypass grafts. For example, the one or more computer systems 102 may be configured to perform CFD simulations under computational resting and stress conditions using modified/new patient-specific reconstructions that were generated at block 206 (i.e., the 3D patient-specific reconstructions including one or more additional path lines associated with virtual bypass grafts).

The patient-specific 3D reconstructions and virtual bypass grafts are configured to computationally simulate hyperemic conditions. The one or more computer systems 102 may be configured to extrapolate a resting flow rate by shortening/truncating its diastolic portion and shifting the resting flow rate up to extrapolate a simulated hyperemic waveform. In some embodiments, the extrapolated simulated hyperemic waveform may be prescribed at an aortic inlet. Furthermore, in embodiments, flow parameters are calculated in the native coronary arteries and virtual bypass grafts. For example, the one or more computer systems 102 may be further configured to calculate the flow parameters based on the CFD studies/simulations. Additionally, the one or more computer systems 102 may be configured to perform post-virtual CABG CFD studies under computational resting and stress conditions and assess hemodynamic impact of virtual CABG on the resting and hyperemic flow of diseased native coronary arteries and virtual bypass grafts using any of the tools and/or techniques described in the examples or embodiments discussed herein.

In an example implementation, the total capacitance may be distributed proportionally to the outlet areas. For each patient, the resistance and capacitance parameters are iteratively adjusted to match the patient's pressure under resting conditions. The resistance and capacitance of each outlet are iteratively adjusted to match the normal aortic root blood pressure. The boundary condition values are tuned until the difference to the target pressure of the aorta is below a threshold difference. The CFD simulations may be run in a computer cluster. In some embodiments, one or more of the following local hemodynamic parameters are calculated: resting distal coronary pressure to aortic pressure ratio (Pd/Pa), FFR, flow rate, flow velocity, time-averaged wall shear stress (TAWSS), and oscillatory shear index (OSI), where the mean pressures used to calculate the resting Pd/Pa and FFR are based on the computationally simulated resting and hyperemic conditions, respectively.

Specific implementations of the computational simulation platform 200 are discussed in certain examples or embodiments discussed herein. However, these examples should not be construed as limitations of the present disclosure, unless otherwise specified in the claims. In other implementations, equivalent systems, tools, materials, software and/or processes may be employed without deviating from the scope of this disclosure. Furthermore, certain aspects or configurations described with respect to a specific embodiment may be implemented in combination with any aspect or configuration of another embodiment without deviating from the scope of this disclosure.

The computational simulation platform 200 presents a comprehensive computational methodology that can reproduce the physiologic effects of bypass grafting on the native coronary bed. An individualized strategy based on non-invasive anatomical imaging (e.g., CCTA) coupled with computational simulations may offer accurate predictions about the hemodynamic interdependence between native arteries and grafts, thereby guiding the revascularization plan (type and number of grafts) and potentially improving the long-term graft patency.

Although the technology has been described with reference to the embodiments illustrated in the attached drawing figures, equivalents may be employed, and substitutions may be made herein without departing from the scope of the technology as recited in the claims. Components illustrated and described herein are examples of devices and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A computer-implemented method for assessing impact of a coronary artery bypass grafting (CABG) procedure, comprising:

reading a plurality of images of a heart of a subject via non-invasive imaging;

reading a resting cardiac cycle of the subject, the resting cardiac cycle comprising a blood flow rate, a first diastolic portion, and a first systolic portion;

extracting blood flow path lines from the plurality of images;

segmenting the path lines to a plurality of lumen contours;

lofting the plurality of lumen contours to create subject-specific three-dimensional geometries of the great vessels including the ascending aorta and the coronary arteries, the subject-specific three-dimensional geometries comprising lumen boundaries, coronary outlets, non-coronary outlets, and an aortic inlet;

discretizing the three-dimensional geometries into polyhedral elements with three refined prism layers;

performing virtual CABG, thereby modifying the subject-specific three-dimensional geometries to include path lines for one or more bypass grafts;

assigning a three-element Windkessel model for non-coronary outlets of the subject-specific three-dimensional geometries and a lumped parameter model for coronary outlets of the subject-specific three-dimensional geometries;

assigning parameters for resistance and capacitance to the lumen boundaries;

generating a second diastolic portion shorter than the first diastolic portion and a second systolic portion;

generating a computationally simulated hyperemic cardiac cycle of the subject comprising the second diastolic portion and second systolic portion;

performing a first post-virtual CABG computational fluid dynamic study under the resting cardiac cycle; and performing a second post-virtual CABG computational fluid dynamic study using the computationally simulated hyperemic cardiac cycle; and assessing hemodynamic impact of virtual CABG on a resting condition and a hyperemic condition of diseased coronary arteries and the virtual bypass grafts based on the first post-virtual CABG computational fluid dynamic study and the second post-virtual CABG computational fluid dynamic study.

2. The computer implemented method of claim 1, wherein the non-invasive imaging comprises computed tomography angiography or magnetic resonance angiography.

3. The computer implemented method of claim 1, wherein the subject-specific three-dimensional geometries and virtual bypass grafts are discretized into a fine mesh near the lumen boundaries.

4. The computer implemented method of claim 1, wherein the computationally simulated hyperemic cardiac cycle is prescribed at an aortic inlet.

5. The computer implemented method of claim 4, wherein parameters for total capacitance are distributed proportionally to coronary and non-coronary outlet areas, wherein the resistance and capacitance parameters are iteratively adjusted to match normal aortic root blood pressure.

6. The computer implemented method of claim 1, wherein the computer-implemented method further includes:

calculating flow parameters in the coronary arteries and virtual bypass grafts including resting distal coronary pressure to aortic pressure ratio (Pd/Pa), fractional flow reserve (FFR), flow rate, flow velocity, time-averaged wall shear stress (TAWSS), and oscillatory shear index (OSI), where mean pressures used to calculate a resting Pd/Pa and FFR are based on the resting cardiac cycle and the computationally simulated hyperemic cardiac cycle, respectively.

7. The computer implemented method of claim 1, wherein the computer-implemented method is configured to guide a surgeon on a number and type of grafts to be used, improve surgical planning, procedural duration, graft patency and clinical outcomes.

8. The computer implemented method of claim 1, wherein the first systolic portion and the second systolic portion are of equal duration.

9. A system for assessing impact of a coronary artery bypass grafting (CABG) procedure, comprising:

one or more medical imaging devices; and a computing node comprising a computer readable storage medium having program instructions embodied therewith, the program instructions executable by a processor of the computing node to cause the processor to perform a method comprising:

reading a plurality of images of a heart of a subject via non-invasive imaging;

reading a resting cardiac cycle of the subject, the resting cardiac cycle comprising a blood flow rate, a first diastolic portion, and a first systolic portion;

extracting blood flow path lines from the plurality of images;

segmenting the path lines to a plurality of lumen contours;

lofting the plurality of lumen contours to create subject-specific three-dimensional geometries of great vessels including the ascending aorta and the coronary arteries, the subject-specific three-dimensional geometries comprising lumen boundaries, coronary outlets, non-coronary outlets, and an aortic inlet;

discretizing the three-dimensional geometries into polyhedral elements with three refined prism layers;

performing virtual CABG, thereby by modifying the subject-specific three-dimensional geometries to include path lines for one or more bypass grafts;

assigning a three-element Windkessel model for non-coronary outlets of the subject-specific three-dimensional geometries and a lumped parameter model for coronary outlets of the subject-specific three-dimensional geometries assigning parameters for resistance and capacitance to the lumen boundaries;

generating a second diastolic portion shorter than the first diastolic portion and a second systolic portion;

generating a computationally simulated hyperemic cardiac cycle of the subject comprising the second diastolic portion and second systolic portion;

performing a first post-virtual CABG computational fluid dynamic study under the resting cardiac cycle; and performing a second post-virtual CABG computational fluid dynamic study using the computationally simulated hyperemic cardiac cycle; and assessing hemodynamic impact of virtual CABG on a resting condition and a hyperemic condition of diseased coronary arteries and the virtual bypass grafts based on the first post-virtual CABG computational fluid dynamic study and the second post-virtual CABG computational fluid dynamic study.

10. The system of claim 9, wherein the noninvasive imaging comprises computed tomography angiography or magnetic resonance angiography.

11. The system of claim 9, wherein the subject-specific three-dimensional geometries and virtual bypass grafts are discretized into a fine mesh near the lumen boundaries.

12. The system of claim 9, wherein the computationally simulated hyperemic cardiac cycle is prescribed at an aortic inlet.

13. The system of claim 12, wherein total capacitance is distributed proportionally to coronary and non-coronary outlet areas, wherein the parameters for resistance and capacitance are iteratively adjusted to match normal aortic root blood pressure.

14. The system of claim 9, wherein the computing node is further configured to:

calculate flow parameters in the coronary arteries and virtual bypass grafts including resting distal coronary pressure to aortic pressure ratio (Pd/Pa), fractional flow reserve (FFR), flow rate, flow velocity, time-averaged wall shear stress (TAWSS), and oscillatory shear index (OSI), where mean pressures used to calculate a resting Pd/Pa and FFR are based on the resting cardiac cycle and the computationally simulated hyperemic cardiac cycle, respectively.

15. The system of claim 9, wherein the first systolic portion and the second systolic portion are of equal duration.

* * * * *